US010745526B2

(12) United States Patent
Daigle et al.

(10) Patent No.: US 10,745,526 B2
(45) Date of Patent: Aug. 18, 2020

(54) CROSSLINKED POLYMER BASED ON A RANDOM COPOLYMER AND A VOLATILE POLYAMINATED CROSSLINKING AGENT AND PROCESSES FOR PRODUCING SAME

(71) Applicant: HYDRO-QUÉBEC, Montréal, Québec (CA)

(72) Inventors: Jean-Christophe Daigle, Longueuil (CA); Serge Verreault, St-Tite (CA); Nancy Turcotte, Varennes (CA); Julie Hâmel-Paquet, Montréal (CA); Karim Zaghib, Longueuil (CA)

(73) Assignee: HYDRO-QUEBEC, Montreal, Quebec (CA)

( * ) Notice: Subject to any disclaimer, the term of this patent is extended or adjusted under 35 U.S.C. 154(b) by 248 days.

(21) Appl. No.: 15/523,875

(22) PCT Filed: Nov. 3, 2015

(86) PCT No.: PCT/CA2015/051127
§ 371 (c)(1),
(2) Date: May 2, 2017

(87) PCT Pub. No.: WO2016/070270
PCT Pub. Date: May 12, 2016

(65) Prior Publication Data
US 2017/0327650 A1    Nov. 16, 2017

(30) Foreign Application Priority Data

Nov. 3, 2014  (CA) .................................... 2870076
Mar. 24, 2015 (CA) .................................... 2886173

(51) Int. Cl.
*C08G 81/02*   (2006.01)
*C08F 220/28*  (2006.01)
(Continued)

(52) U.S. Cl.
CPC .......... *C08G 81/025* (2013.01); *C07C 211/18* (2013.01); *C08F 6/28* (2013.01);
(Continued)

(58) Field of Classification Search
None
See application file for complete search history.

(56) References Cited

U.S. PATENT DOCUMENTS

2008/0166636 A1*  7/2008  Niitani ................. C08F 290/06
                                                  429/317

FOREIGN PATENT DOCUMENTS

EP    0158881 A2 *  10/1985  ................ C08F 8/32
EP    0158881 A2     10/1985
(Continued)

OTHER PUBLICATIONS

Extended European Search Report dated May 14, 2018, issued by the European Patent Office in corresponding European Application No. 15857881.5-1102 (8 pages).
(Continued)

*Primary Examiner* — Rachel Kahn
*Assistant Examiner* — Ha S Nguyen
(74) *Attorney, Agent, or Firm* — Buchanan Ingersoll & Rooney P.C.

(57) ABSTRACT

Crosslinked polymers and their uses in electrochemical systems, for example, as electrolyte membrane, are described. More precisely, these crosslinked polymers are formed by the crosslinking of a random copolymer based on monomers of glycidyl methacrylate or acrylate and of poly (ethylene glycol) methyl acrylate or methacrylate with a volatile polyamine crosslinking agent.

21 Claims, 6 Drawing Sheets

(51) Int. Cl.
| | |
|---|---|
| *H01M 10/0565* | (2010.01) |
| *C08F 290/06* | (2006.01) |
| *C08F 8/32* | (2006.01) |
| *C08F 6/28* | (2006.01) |
| *C08J 3/24* | (2006.01) |
| *C08F 20/18* | (2006.01) |
| *C07C 211/18* | (2006.01) |
| *C08F 220/32* | (2006.01) |
| *H01M 10/052* | (2010.01) |
| *C08L 55/00* | (2006.01) |
| *C08K 5/17* | (2006.01) |

(52) U.S. Cl.
CPC .............. *C08F 8/32* (2013.01); *C08F 20/18* (2013.01); *C08F 220/28* (2013.01); *C08F 290/062* (2013.01); *C08J 3/24* (2013.01); *H01M 10/0565* (2013.01); *C08F 220/325* (2020.02); *C08F 2500/01* (2013.01); *C08F 2810/20* (2013.01); *C08J 2333/14* (2013.01); *H01M 10/052* (2013.01); *H01M 2300/0085* (2013.01)

(56) References Cited

FOREIGN PATENT DOCUMENTS

| | | |
|---|---|---|
| EP | 1 847 556 | 10/2007 |
| JP | 03238704 A * | 10/1991 |
| JP | H0629043 A | 2/1994 |
| WO | WO 2005/014698 A1 | 2/2005 |
| WO | WO-2005014698 A1 * | 2/2005 ........... A61K 9/5026 |

OTHER PUBLICATIONS

International Search Report (PCT/ISA/210) dated Dec. 21, 2015, by the Canadian Patent Office as the International Searching Authority for International Application No. PCT/CA2015/051127.

Written Opinion (PCT/ISA/237) dated Dec. 21, 2015, by the Canadian Patent Office as the International Searching Authority for International Application No. PCT/CA2015/051127.

Luo, D. et al, "Preparation and characterization of novel crosslinked Poly[glycidyl methacrylate-poly( ethylene glycol) methyl ether methacrylate] as gel polymer electrolytes", Journal of Applied Polymer Science, vol. 120 , No. 5, pp. 2979-2984, 2011.

Koo, G. H. et al.,"Depth-Gradient and Photoinitiator-Free Photocrosslinking of Poly(ethylene oxide)", Journal of Applied Polymer Science, vol. 12, No. 4, pp. 2659-2667, 2012.

Shyichuk, A. V. et al., "Comparison of UV-degradation depth-profiles in polyethylene, polypropylene and an ethylene-propylene copolymer", Polymer Degradation and Stability, vol. 88, No. 3, pp. 415-419, 2005.

Benaglia, M. et al., "Poly(glycidly methacrylate): a highly versatile polymeric building block for post-polymerization modifications", Polym. Chem., vol. 4, No. 1, pp. 124-132, 2013.

Gadwal, I. et al., "Functionalized Molecular Bottlebrushes", Macromolecules, vol. 47, No. 1, pp. 35-40, 2013.

Enns, J. B. et al., "Effect of the Extent of Cure on the Modulus, Glass Transition, Water Absorption, and Density of an Amine-Cured Epoxy", Journal of Applied Polymer Science, vol. 28, No. 9, 2831-2846, 1983.

Jordan, C. et al., "Measurement of the Extent of Reaction of an Epoxy-Cycloaliphatic Amine System and Influence of the Extent of Reaction on Its Dynamic and Static Mechanical Properties", Journal of Applied Polymer Science, vol. 46, No. 5, pp. 859-871, 1992.

Tillet, G. et al., "Chemical reactions of polymer crosslinking and post-crosslinking at room and medium temperature", Progress in Polymer Science, vol. 36, No. 2, pp. 191-217, 2011.

Monroe, C. et al., "The Effect of Interfacial Deformation on Electrodeposition Kinetics", Journal of the Electrochemical Society, vol. 151, No. 6, pp. A880-A886, 2004.

Monroe, C. et al., "The Impact of Elastic Deformation on Deposition Kinetics at Lithium/Polymer Interfaces", Journal of the Electrochemical Society, vol. 151, No. 6, pp. A396-A404, 2005.

Patil, P. et al., "Free Volumes and Structural Relaxations in Diglycidyl Ether of Bisphenol-A Based Epoxy-Polyether Amine Networks", Soft Matter, vol. 3, pp. 3589-3599, 2013.

Sindt, O. et al., "Molecular Architecture-Mechanical Behaviour Relationships in Epoxy Networks", Polymer, vol. 37, No. 14, pp. 2989-2997, 1996.

Office Action (Notice of Reasons for Rejection) dated Nov. 20, 2019, by the Japanese Patent Office in corresponding Japanese Patent Application No. 2017-523470, and an English Translation of the Office Action. (6 pages).

Office Action (Examination report under sections 12 & 13 of the Patents Act, 1970 and the Patents Rules, 2003.) dated Jun. 12, 2019, by the Indian Patent Office in corresponding Indian Patent Application No. 201717012144, and an English Translation of the Office Action. (5 pages).

Siegwart, D. J. et al."Combinatorial synthesis of chemically diverse core-shell nanoparticles for intracellular delivery" vol. 108. No. 32, Aug. 9, 2011, pp. 12996-13001.

\* cited by examiner

CROSSLINKED POLYMER BASED ON A RANDOM COPOLYMER AND A VOLATILE POLYAMINATED CROSSLINKING AGENT AND PROCESSES FOR PRODUCING SAME

TECHNICAL FIELD

The application relates to the field of polymers and their use in electrochemical applications. More particularly, the technology relates to the field of crosslinked random copolymers.

BACKGROUND

One of the problems encountered when using membranes in lithium-polymer batteries is with respect to their degradation over time. This phenomenon is particularly important when using radical crosslinking agents activated chemically or by photochemistry during the formation of a crosslinked membrane to increase its mechanical strength. Indeed, the formation of free radicals in the polymeric structure causes degradation of the membrane by extraction of the protons present on the main chain, thereby causing chain scission mechanism. This phenomenon is particularly important during the use of UV light for initiating the reaction (see Koo, G.-H. et al, *J. Appl. Polym. Sc.* 2012, 125 (4), 2659-2667; and Shyichuk, A. V. et al, *Polymer Degradation and Stability* 2005, 88 (3), 415-419).

Chemical crosslinking by reaction of an amine with an oxirane group is common in the world of epoxy-type coatings and draws more and more of the attention of chemists due to its great reactivity (see Benaglia, M. et al, *Polym. Chem.* 2013, 4 (1), 124-132; and Gadwal, I. et al, *Macromolecules*, 2013, 47 (1), 35-40). These materials, commonly called thermosetting materials, are of interest because of their hardening which increases both their chemical and mechanical resistance (see Enns, J. B. et al, *J. Appl. Polym. Sc.*, 1983, 28 (9), 2831-2846; and Jordan, C. et al, *J. Appl. Polym. Sc.*, 1992, 46 (5), 859-871).

A literature review shows that there are several types of chemical crosslinking reactions. Most lead to the formation of unwanted by-products such as water or acids. Other reactions are carried out at high temperature or in the presence of a copper-based inorganic catalyst (for example, see Tillet, G. et al, *Prog. Polym. Sc.*, 2011, 36 (2), 191-217). These various residual elements are not desirable in an electrochemical system.

Several amine crosslinking agents are present on the market. However, these are not very volatile and remain trapped in the polymer, the crosslinking reactions not being 100% completed in order to obtain optimum mechanical properties (see Jordan et al, *Supra*).

It has been demonstrated that the use of a Jeffamine®-type crosslinking agent for the formation of gel-like membranes for the ionic conduction of lithium allows for the formation of a crosslinked polymer (see, for example, Luo, D. et al, *J. Appl. Polym. Sc.* 2011, 120 (5), 2979-2984). It is however possible that these free crosslinking agents react during battery cycling thereby causing an accelerated degradation of the lithium anode and/or of the gel electrolyte by migration of compounds from the membrane to the anode. Moreover, the presence of free Jeffamine increases the elasticity of the membrane and reduces its mechanical properties by a plasticizer effect.

SUMMARY

The present application relates to a crosslinked polymer made from a random copolymer based on glycidyl methacrylate or acrylate (Monomer A) and poly(ethylene glycol) methyl acrylate or methacrylate (Monomer B) (random copolymer) and a volatile polyamine crosslinking agent. In other words, the crosslinked polymer is derived from the crosslinking of the random copolymer in the presence of the volatile polyamine crosslinking agent. The technology also relates to the use of the crosslinked polymer in electrochemical applications. For instance, the crosslinked polymers of the present application may be used in the preparation of solid electrolyte membranes for electrochemical cells.

According to a first aspect, the random copolymer is of Formula I:

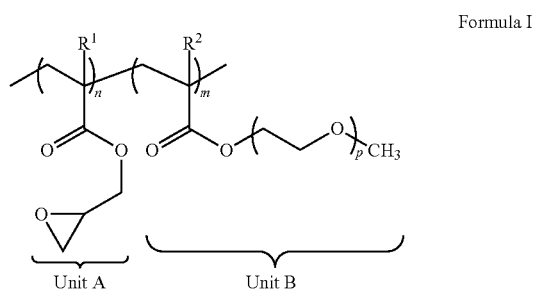

Formula I wherein:
$R^1$ and $R^2$, independently at each occurrence, is a hydrogen atom or a methyl group;
n is an integer and is such that units A (derived from Monomer A) represent from 10 to 45% molar of the copolymer composition;
m is an integer and is such that units B (derived from Monomer B) represent from 55 to 90% molar of the copolymer composition, where n+m=100%; and
p is an integer and defines the number of ethylene glycol units present in unit B and is between 2 and 30 or is such that unit B has a number molar weight between 200 and 1000 g/mol, or between 250 and 600 g/mol, or between 400 and 750 g/mol, or between 400 and 600 g/mol;
the random copolymer of Formula I having a number molar weight between 100 000 and 400 000 g/mol, limits included.

According to one example, $R^1$ is a methyl group and $R^2$ is a hydrogen atom at each occurrence. According to another example, $R^1$ and $R^2$ are methyl groups at each occurrence.

According to one embodiment, the random copolymer is of Formula II, defined as follows:

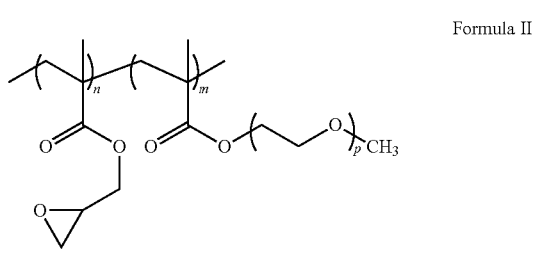

Formula II

Preferably, the random copolymer of Formula II has a number molar weight between 100 000 and 400 000 g/mol limits included; n is an integer and is such that unit A (GMA) represents from 10 to 45% molar of the copolymer composition; m is an integer and is such that unit B (PEGMA) represents from 55 to 90% molar of random copolymer composition, where n+m=100%; and p is an integer and defines the number of ethylene glycol units present in unit B and is between 2 and 30, for example, unit B has a number molar weight between 200 and 1000, or between 250 and 600, or between 400 and 750, or between 400 and 600.

For example, the random copolymer of Formula I or II may comprise a molar ratio unit A:unit B between 15:85 and 45:55 limits included, a molar ratio between 30:70 and 45:55 limits included, or a molar ratio of about 39:61. For instance, the number molar weight of the random copolymer of Formula I or II is within the range of from 100 000 to 250 000 g/mol limits included and unit A represents from 15 to 35 mole %, or the number molar weight of the copolymer is whit in the range of from 250 000 to 400 000 g/mol limits included and unit A represents from 35 to 45 mole % of the copolymer composition. According to another example, the number molar weight of the random copolymer is between 280 000 and 360 000 g/mol and unit A represents about 39 mole % of the copolymer composition.

The random copolymer of Formula I or II may be previously formed by the copolymerization of the following Monomers A and B:

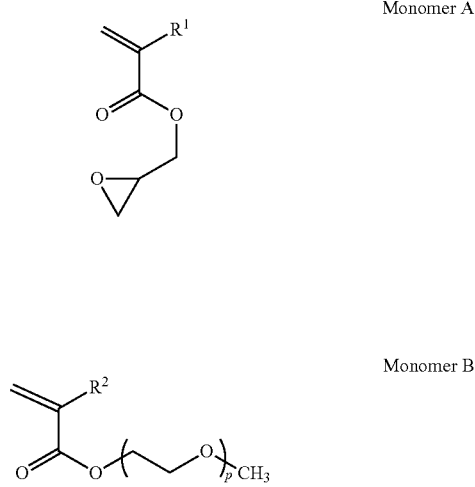

where $R^1$, $R^2$ and the variable p are as defined above. According to one example, $R^1$ is a methyl group. According to another example, $R^1$ is a hydrogen atom. According to one example, $R^2$ is a methyl group. According to another example, $R^2$ is a hydrogen atom. According to one embodiment, $R^1$ et $R^2$ are identical, for example, both of them are methyl groups.

The crosslinking agent is a volatile alkyl polyamine compound, for example including from 1 to 3 carbon(s), preferably 1 or 2 carbon(s), and at least two amine groups, the crosslinking agent having a boiling point of less than 150° C. Examples of crosslinking agents include ethylenediamine, 1,3-diaminopropane, 1,2-diaminopropane and their mixtures, preferably, the crosslinking agent is ethylenediamine.

According to another aspect, the present application relates to a process for the preparation of a crosslinked polymer as defined in the present application, which includes the steps of: (a) mixing the random copolymer of Formula I or II and the polyamine crosslinking agent, optionally in a solvent; (b) crosslinking, preferably by heating; and (c) elimination of the residual volatile polyamine crosslinking agent and, eventually of the solvent, by evaporation, for example, by heating under vacuum, steps (b) and (c) may be performed simultaneously or in sequence. Preferably, step (a) includes from 5 to 10 equivalents of the crosslinking agent as a function of the oxirane groups of units A. According to another example, the crosslinking agent may also be used in excess and act as a solvent, i.e. without requiring the addition of additional solvent in the step (a). The process may further include a step of spreading the mixture from the step (a) on a support prior to its crosslinking.

When step (a) includes the addition of a solvent (other than the crosslinking agent), the process may include an elimination step of this solvent prior to step (b), which may be performed by heating at atmospheric pressure, for example, at a temperature between 50 and 100° C., preferably between 60° C. and 90° C. For example, the solvent is selected from lower alcohols (such as methanol, ethanol, isopropanol and/or n-propanol), water, and their mixture, preferably a solvent which includes a lower alcohol such as ethanol.

DETAILED DESCRIPTION

Figure 1:
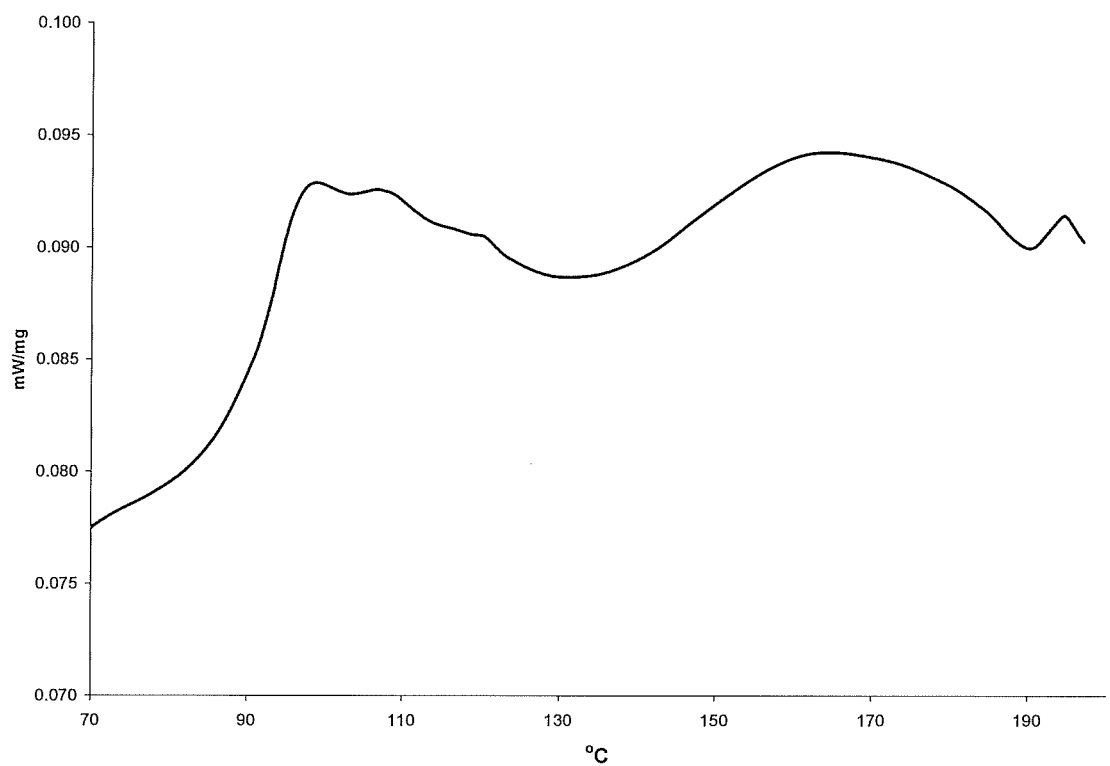
FIG. 1 displays the DSC reaction profile between the copolymer PEGMA-GMA (39 mol % GMA, 61 mol % PEGMA, molecular weight: 320 000 g/mol) and the crosslinking agent.

The following detailed description and examples are illustrative and should not be interpreted as further limiting the scope of the invention.

The term «about» as used in the present document means approximately, in the region of, and around. Where the term «about» is used in connection with a numerical value, it modifies the value by a variation of 10% above and below in comparison to the nominal value. This term may also take into account, for example, the experimental error of the measuring instrument.

The present application relates to the use of a random copolymer based on glycidyl methacrylate or acrylate (Monomer A) and poly(ethylene glycol) methyl acrylate or methacrylate (Monomer B) (random copolymer) and a volatile polyamine crosslinking agent for the formation of a crosslinked polymer. The technology also relates to the crosslinked polymer thus formed and its use in electrochemical applications. For example, for the formation of solid electrolyte membranes used in electrochemical cells.

According to the first aspect, the random copolymer is of Formula I

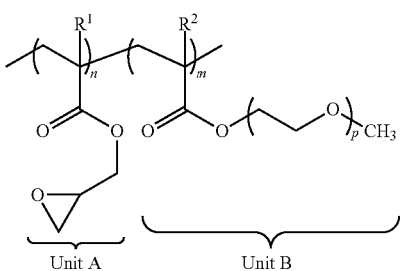

Formula I

Unit A    Unit B wherein:
$R^1$ and $R^2$, independently and at each occurrence, is a hydrogen atom or a methyl group;
n is an integer and is such that units A (derived from Monomer A) represent from 10 to 45% molar of the copolymer composition;
m is an integer and is such that units B (derived from Monomer B) represent from 55 to 90% molar of the copolymer composition, where n+m=100%; and
p is an integer and defines the number of ethylene glycol units present in unit B and is between 2 and 30 or is such that the unit B has a number molar weight between 200 and 1000 g/mol, or between 250 and 600 g/mol, or between 400 and 750 g/mol, or between 400 and 600 g/mol, limits included; the random copolymer of Formula I having a number molar weight between 100 000 and 400 000 g/mol, limits included.

According to one example, $R^1$ is a methyl group and $R^2$ is a hydrogen atom at each occurrence. According to another example, $R^1$ and $R^2$ both are a methyl group at each occurrence.

According to one embodiment, the random copolymer is of Formula II, defined as follows:

Formula II

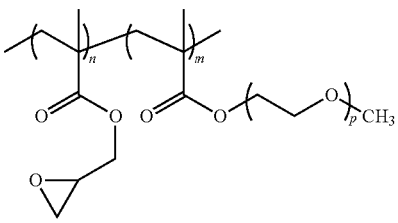

Preferably, the random copolymer of Formula II possesses a number molar weight between 100 000 and 400 000 g/mol; where n is an integer and represents the number of units A (GMA) such that these compose between 10 to 45% molar of the copolymer composition; where m is an integer and represent the number of units B (PEGMA) such that these compose between 55 and 90% molar of the copolymer composition, and where n+m=100%; and where p is an integer and defines the number of ethylene glycol units present in unit B and is between 2 and 30. For example, the unit B has a number molar weight between 200 and 1000, or between 250 and 600, or between 400 and 750, or again between 400 and 600.

According to one example, the random copolymer of Formula I or II includes a unit A:unit B molar ratio between 15:85 and 45:55 limits included, a unit A:unit B molar ratio between 30:70 et 45:55, or a molar ratio of about 39:61. For instance, the number molar weight of random copolymer of Formula I or II is in the range between 100 000 to 250 000 g/mol limits included and the unit A represents from 15 to 35% in mole, or the molecular weight by number of the random copolymer is within the range of from 250 000 to 400 000 g/mol limits included and the unit A represents from 35 to 45 mole % of the copolymer composition. For example, the number molar weight of random copolymer may be between 280 000 and 360 000 g/mol and the unit A represents about 39 mole % of the copolymer's composition.

The random copolymer of Formula I or II is, for example, previously formed by random copolymerization of the following Monomers A and B:

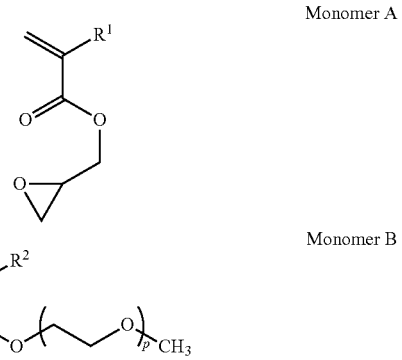

Monomer A

Monomer B where $R^1$, $R^2$ and p are as defined above.

The crosslinking agent added to the random polymer of Formula I or II is a volatile alkyl polyamine compound, for example comprising from 1 to 3 carbon(s), preferably 1 or 2 carbon(s), and at least two amine groups, the crosslinking agent preferably having a boiling point of less than 150° C. Examples of crosslinking agents include ethylenediamine, 1,3-diaminopropane, 1,2-diaminopropane or their mixtures, preferably, the crosslinking agent is ethylenediamine. Advantageously, the diamine compounds have 4 protons, which allows for the crosslinking of 4 oxirane functions. Moreover, their low boiling point, i.e. about 116° C. for the ethylenediamine, facilitates the evaporation of the residues after crosslinking.

Figure 6:
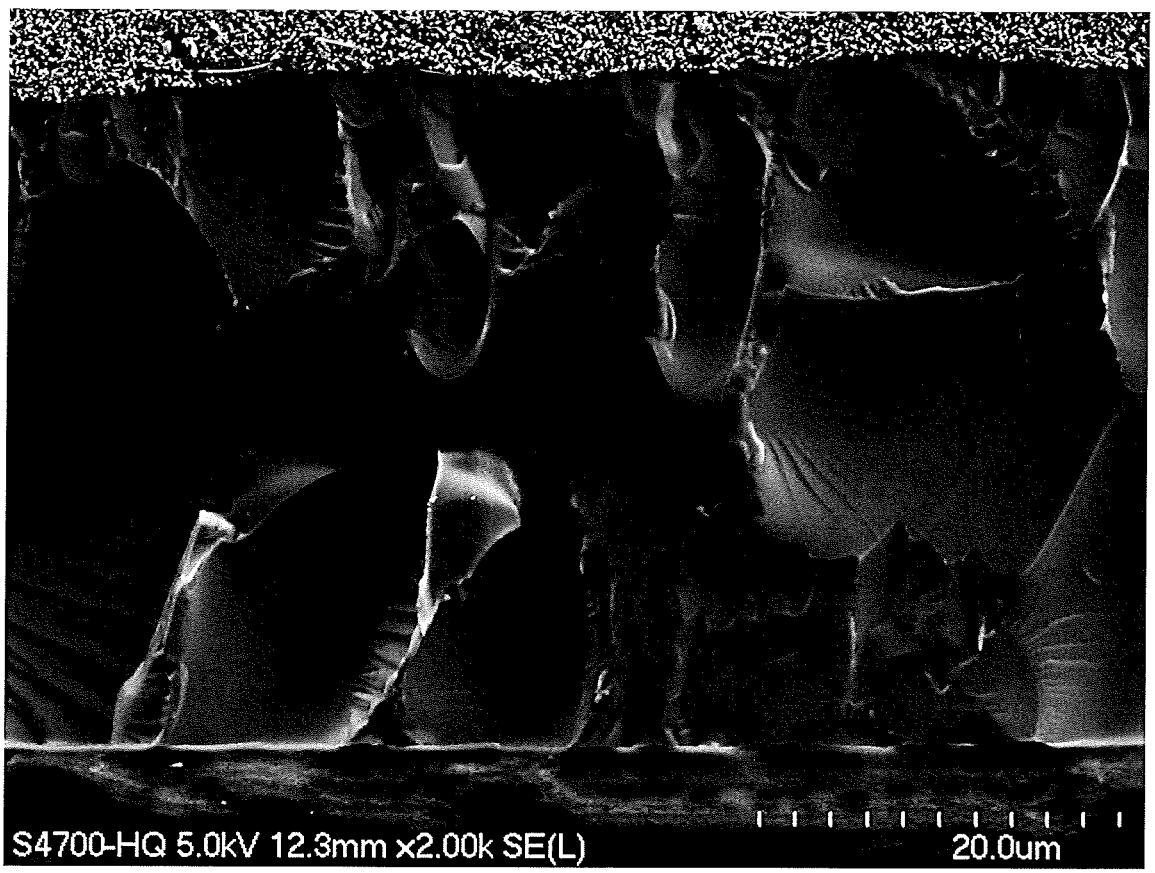
FIG. 6 display a SEM image (5000×, SE(L) detector) of the electrolyte membrane illustrating its great hardness.

The crosslinked polymer of the present application allows to obtain solid electrolyte materials possessing a significant hardness (see FIG. 6). Without wishing to be bond by theory, since the crosslinking agent used in the present application possesses a short carbon chain, this increases significantly the mechanical properties (Young's modulus, shear modulus, etc.) of the crosslinked polymer taking in account the rigidity of the carbon chain which serves for the crosslinking and increase in crosslinking density (Sindt et al, 1996, *Polymer*, 37(14), 2989-97, and Patil et al., 2013, *Soft Matter*, 9, 3589-3599). Thus, the use of volatile crosslinking agents (of low molecular weight) such as in the present application, compared to Jeffamine-type agents may make it possible to increase the shear modulus of the polymer. This property is considered as essential to prevent the formation of lithium dendrites (Singh et al, 2007, *Macromolecules*, 40, 4578-4548; Monroe et al, 2004, *J. Electrochem. Soc.*, 151(6), A880-A886; and Monroe et al, 2005, *J. Electrochem. Soc.*, 152(2), A396-A404).

The present technology also relates to a process for the preparation of a crosslinked polymer as defined in the present application, which includes the steps of: (a) mixing of the random copolymer of Formula I or II and the volatile polyamine crosslinking agent, optionally in a solvent; (b)

crosslinking (for example, by heating); and (c) elimination of residual volatile compounds, including the volatile polyamine crosslinking agent and eventually the solvent, by evaporation (for example, by heating under vacuum), steps (b) and (c) may be performed simultaneously or in sequence. Preferably, step (a) includes from 5 to 10 equivalent of the crosslinking agent as a function of the oxirane groups from units A. According to one example, the crosslinking agent may also be added in excess and serve as a solvent, i.e. without the addition of an additional solvent at step (a).

When step (a) includes the addition of a solvent, the process may include a solvent elimination step prior to step (b), which may be performed by heating at atmospheric pressure, for example, at a temperature between 50 to 100° C., preferably between 60° C. and 90° C. The drying temperature makes it possible, for example, to eliminate the solvent while preserving the higher boiling point crosslinking agent in the composition. Examples of solvents comprise lower alcohols (such as methanol, ethanol, isopropanol and/or n-propanol), water, or their mixtures, preferably a lower alcohol such as ethanol.

The mixture from step (a) may also contain other components such as lithium salts when used as an electrolyte membrane. This mixture could also serve as a matrix for an electrochemically active material such as, for example, in a cathode. In that case, the electrochemically active material may be added to the mixture of step (a) and optionally include a conductive material.

The crosslinking step by heating is preferably performed after spreading of the mixture obtained in step (a) on a support. This spreading may be performed by usual methods in the field of electrochemistry, for example by the « Doctor blade » method. The support may be, for example, a polymer film or a battery component such as a cathode material prepared as a film. For example, the support is a polymer film and may be removed after the step (c).

The crosslinking step may be performed at a temperature of at least 60° C., or between 70 and 200° C., preferably between 80 and 180° C. The polymer thus crosslinked is then dried to remove any trace of volatile compound, including the volatile polyamine crosslinking agent, as well as traces of the solvent used during the mixing step as the case may be. The elimination is carried out at a temperature above the boiling point of the crosslinking agent at the pressure used (e.g. under vacuum). The drying may include an initial heating step at normal pressure followed by a drying step performed by heating under vacuum.

Example 1: Preparation of a Copolymer of Formula I a) Preparation of the Reagents A solution of poly(ethylene glycol) methyl methacrylate (PEGMA, $M_n$=500, Sigma-Aldrich 447943) in toluene is passed over a bed of basic aluminum oxide ($Al_2O_3$). The concentration of the solution was determined after purification by $^1H$ NMR. The glycidyl methacrylate (GMA) is also passed over a bed of basic $Al_2O_3$. Azobisisobutyronitrile (AIBN) is purified by recrystallization in methanol dried under vacuum for 12 hours. The monomers are used immediately after purification. All other chemical products, which come from, for instance, Sigma Aldrich, are used as received.

b) Copolymerization of GMA and PEGMA

A solution of 22.0 g of PEGMA in toluene (32 mol %) and of 1.0 g of GMA is introduced in a 50-mL round-bottomed flask. The solution is stirred for 30 minutes under nitrogen atmosphere. The round-bottomed flask is connected to a condenser and 50.0 mg of AIBN is added. The solution is heated to 80° C. under nitrogen for 8 hours, then cooled and poured into 10 volumes of cold diethyl ether. The viscous polymer is precipitated and the supernatant is decanted. The polymer is poured a second time in 10 volumes of hexanes and the supernatant is again decanted. The polymer is dried at 60° C. under vacuum for 12 hours.

A standard result obtained is a 75% conversion with a 4.5 g yield. According to this example, the insertion of GMA is of 30 mol % and the molecular weight is 100 000 g/mol.

The same process is used, including an adjustment of the initial reagents quantities, for the preparation of a copolymer having a molecular weight of 140 000 g/mol and a GMA insertion rate of about 18 mol %, and of a copolymer having a molecular weight of 320 000 g/mol and a GMA insertion rate of about 39 mol %.

Example 2: Preparation of a Crosslinked Polymer

The preparation of a crosslinked polymer is done in a cleanroom environment with a dew point of −56° C. The copolymer PEGMA-GMA prepared in Example 1 is first dissolved into a minimum of dry ethanol, in order to obtain the right viscosity, thus allowing for the casting on a polypropylene film. For example, 1.92 g of the polymer of $M_n$=100 000 g/mol is dissolved in 2.0 ml of ethanol. After dissolution, 0.27 g of LiTFSI (ratio 30:1, Li:O) is added to the mixture and the solution is stirred at 60° C. for 2 hours. 0.155 g of ethylenediamine is then added to the mixture. The mixture is stirred for 15 minutes and then casted on a polypropylene film (200 μm) by the Doctor Blade method. The film is dried and then crosslinked at 60° C. for 12 hours. The heating temperature is increased to 120° C. for a period of 6 hours. Finally, the film is maintained at 120° C. under vacuum for a period of 6 additional hours to insure the complete evaporation of residual ethylenediamine.

An example of reaction profile between the polymer and the ethylenediamine is presented in FIG. 1 (copolymer having a molecular weight of 320 000 g/mol, 39 mol % GMA, and 61 mol % PEGMA). In this case, the crosslinking reaction occurs between 98° C. and 165° C. and results in a Tg of 171° C. after crosslinking, illustrating an increase in mechanical strength.

Example 3: Capacity of the Crosslinked Polymer

A battery using an electrolyte membrane composed of the polymer presented in Example 2 has a capacity of between 130 and 150 mAh/g at 80° C. The cathode of the battery tested includes carbon coated $LiFePO_4$ and a PEO-based polymer binder. The anode of the battery is a lithium film with a thickness of 45 μm.

The cycling is optimal at a C/6 rate. Moreover, at this rate, the batteries are stables for a period of over 100 cycles with minimal capacity loss. The capacity is a function of the molecular weight of the polymer and the GMA ratio. The best results under these conditions were obtained with a polymer having a molecular weight of 320 000 g/mol and 39 mol % of GMA. The formation of lithium dendrites was not observed.

Figure 3:
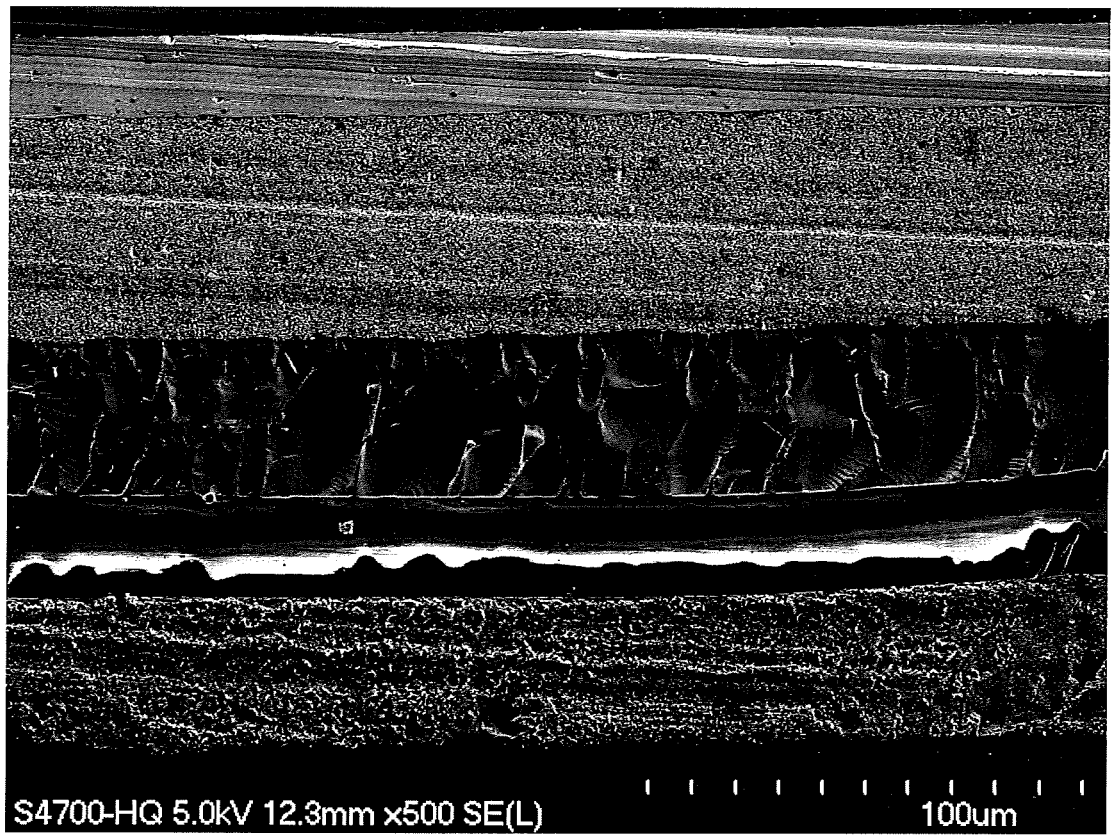
FIGS. 3 and 4 display the images of a vertical cut of the battery presented in Example 3 after cycling, the images were obtained by scanning electron microscopy (500×) with: a SE(L) detector (FIG. 3) and YAG BSE detector (FIG. 4).
Figure 4:
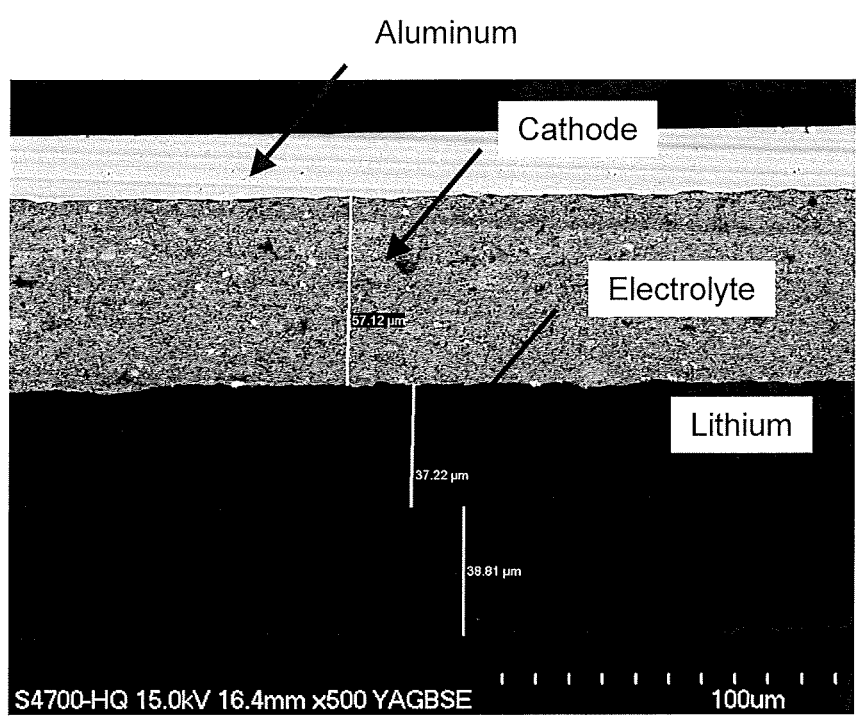
Figure 5:
FIG. 5 displays a SEM image (5000×, YAG BSE detector) of the interface between the lithium (in black) and the electrolyte membrane (in light gray).

In fact, the images of a vertical cut of this battery (after cycling) done by scanning electron microscopy (SEM) are presented in FIGS. 3 to 6. FIGS. 3 and 4 clearly show the preservation of the integrity of the battery. The zoom shown in FIG. 5 demonstrates that the lithium (in black in this figure) does not cross the electrolyte membrane (in light grey in this figure) and therefore, no formation of lithium dendrites is observed. In FIG. 6, the presence of deformation zones, due to the pressure applied during battery preparation, demonstrate the high hardness of the electrolyte membrane.

Example 4: Thermal Stability of the Crosslinked Polymer

Figure 2:
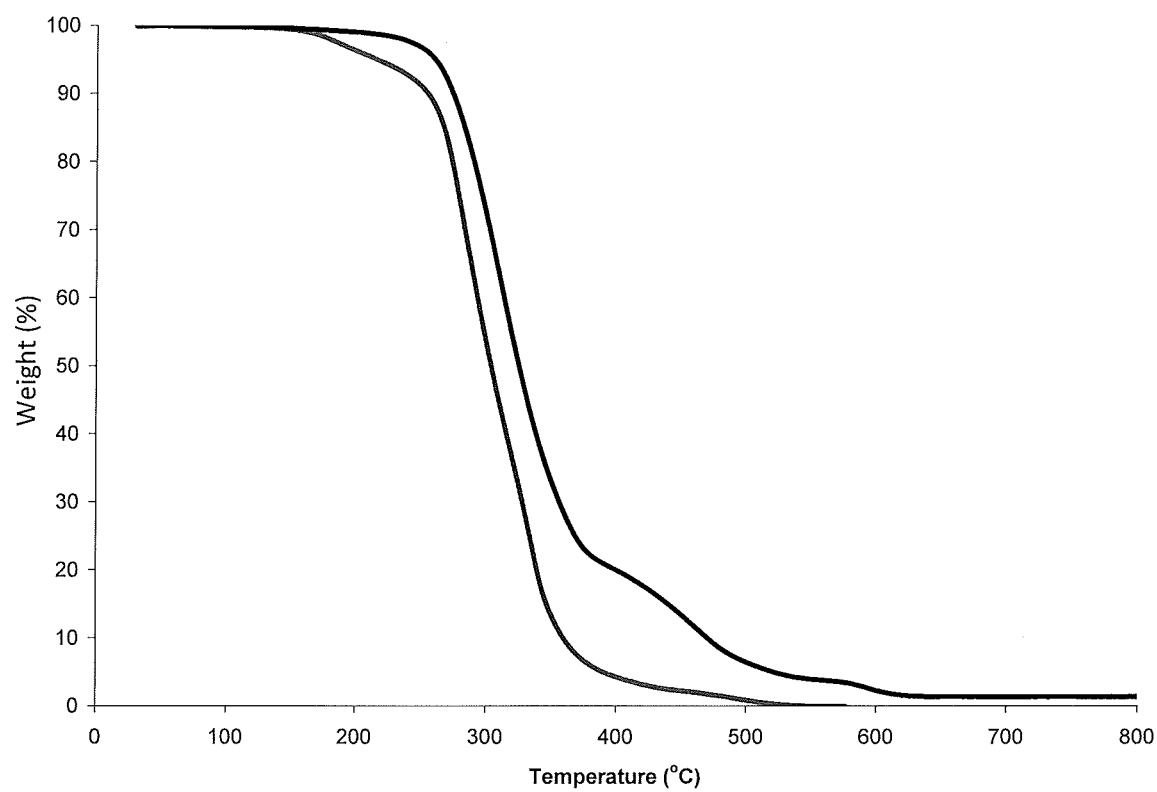
FIG. 2 displays the mass variation as a function of the temperature for the polymer presented in Example 2 prior to crosslinking (left curve) and after crosslinking (right curve).

The improvement in mechanical strength by crosslinking is demonstrated by a decrease in the degradation rate at a given temperature. The thermogravimetric analysis presented in FIG. 2 shows the degradation of two polymers as a function of temperature. The left curve corresponds to the polymer without crosslinking with 39 mol % of GMA and a $M_n$ of 320 000 g/mol. The right curve corresponds to the same polymer after crosslinking. An increase of between 6-18° C. in the degradation temperature is observed.

It may be observed that, at 250° C., the crosslinked polymer retained 97% of its integrity in comparison to the non-crosslinked polymer, which retained only 91%. At elevated temperature, this difference in stability is even greater. No significant mass loss is observed between 120-150° C. for the crosslinked polymer, demonstrating the complete evaporation of the ethylenediamine (boiling point of 116° C.) during the film formation. This also supports the fact that the membrane does not contain any residual cross-linking agent.

The invention claimed is:

1. A solid polymer electrolyte for use in an electrochemical cell, the solid polymer electrolyte comprising a crosslinked polymer consisting of a random copolymer based on glycidyl methacrylate or acrylate (Monomer A) and of poly(ethylene glycol) methyl acrylate or methacrylate (Monomer B) and of a volatile polyamine crosslinking agent, wherein the volatile polyamine crosslinking agent has a boiling point less than 150° C., wherein the random copolymer is of Formula I:

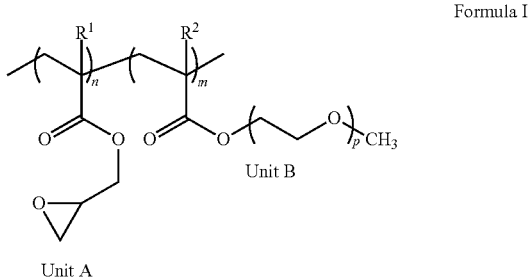

Formula I wherein:
$R^1$ and $R^2$, independently at each occurrence, is a hydrogen atom or a methyl group;
n is such that units A (derived from Monomer A) represent from 10 to 45% molar of the copolymer composition;
m is such that units B (derived from Monomer B) represent from 55 to 90% molar of the copolymer composition, where n+m=100%; and
p defines the number of ethylene glycol units present in unit B and is between 2 and 30, limits included, or is such that unit B has a number molar weight between 200 and 1000 g/mol, limits included;
the random copolymer of Formula I having a number molar weight between 100 000 and 400 000 g/mol, limits included.

2. The solid polymer electrolyte according to claim 1, wherein $R^1$ is a methyl group and $R^2$ is a hydrogen atom.

3. The solid polymer electrolyte according to claim 1, wherein the random copolymer is of Formula II:

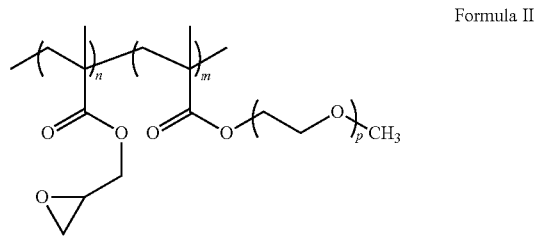

Formula II wherein:
n, m and p are as defined in claim 1;
the random copolymer of Formula II having a number molar weight between 100 000 and 400 000 g/mol, limits included.

4. The solid polymer electrolyte according to claim 1, wherein the number molar weight of the random copolymer is in the range of from 100 000 to 250 000 g/mol, limits included, and unit A represents from 15 to 35 mol % of the random copolymer composition.

5. The solid polymer electrolyte according to claim 1, wherein the number molar weight of the copolymer is in the range of from 250 000 to 400 000 g/mol, limits included, and unit A represents from 35 to 45 mol % of the copolymer composition.

6. The solid polymer electrolyte according to claim 1, wherein the number molar weight of the random copolymer is between 280 000 to 360 000 g/mol and unit A represents about 39 mol % of the copolymer composition.

7. The solid polymer electrolyte according to claim 1, wherein the crosslinking agent is an alkyl compound comprising 1 or 2 carbon(s), and at least two amine groups.

8. The solid polymer electrolyte according to claim 1, wherein the crosslinking agent is ethylenediamine, 1,3-diaminopropane, 1,2-diaminopropane or a mixture of at least two of the crosslinking agents.

9. The solid polymer electrolyte according to claim 8, wherein the crosslinking agent is ethylenediamine.

10. A process for the preparation of a solid polymer electrolyte as defined in claim 1, which comprises the following steps:
(a) mixing of the random copolymer and the volatile polyamine crosslinking agent;
(b) crosslinking of the mixture obtained in step (a); and
(c) elimination of the residual volatile polyamine crosslinking agent by evaporation, steps (b) and (c) being performed simultaneously or in sequence.

11. The process according to claim 10, which further comprises a step of spreading the mixture obtained in step (a) on a support.

12. The process according to claim 10, which comprises the addition of a solvent in step (a).

13. The process according to claim 12, wherein the solvent comprises a lower alcohol, water, or a mixture of the lower alcohol and water.

14. The process according to claim 13, wherein the solvent is a lower alcohol selected from methanol, ethanol, isopropanol, n-propanol and their mixtures.

15. The process according to claim 14, wherein the solvent is ethanol.

16. The process according to claim 12, which further comprises a solvent evaporation step prior to the crosslinking step (b), by evaporation under atmospheric pressure at a temperature between 50 and 100° C.

17. The process according to claim 10, wherein the crosslinking step (b) comprises a heating step.

18. The process according to claim 10, wherein step (c) comprises a step of evaporation by heating under vacuum.

19. The process according to claim 16, wherein the solvent evaporation step is at a temperature between 60 and 90° C.

20. The solid polymer electrolyte according to claim 1, further comprising a lithium salt.

21. The process according to claim 10, wherein step (a) further comprises a lithium salt.

\* \* \* \* \*